United States Patent [19]

Wiksell

[11] Patent Number: 5,231,976
[45] Date of Patent: Aug. 3, 1993

[54] APPARATUS FOR TRIGGERING SHOCK WAVES

[76] Inventor: Hans Wiksell, Odlingsvägen 7, S-183 44 Täby, Sweden

[21] Appl. No.: 761,815
[22] PCT Filed: Mar. 21, 1990
[86] PCT No.: PCT/SE90/00182
 § 371 Date: Sep. 20, 1991
 § 102(e) Date: Sep. 20, 1991
[87] PCT Pub. No.: WO90/11052
 PCT Pub. Date: Oct. 4, 1990

[30] Foreign Application Priority Data

Mar. 21, 1989 [SE] Sweden ............... 8900995

[51] Int. Cl.⁵ ...................... A61B 17/22
[52] U.S. Cl. .................. 128/24 EL; 367/147; 181/113
[58] Field of Search ............ 128/24 EL, 24 AA; 367/147, 171; 181/113

[56] References Cited

U.S. PATENT DOCUMENTS

| | | | |
|---|---|---|---|
| 3,744,479 | 7/1973 | Stein et al. | 128/24 AA |
| 4,693,247 | 9/1987 | Brisson et al. | 128/24 EL |
| 4,727,875 | 3/1988 | Dory | 128/24 EL |
| 4,734,894 | 3/1988 | Cannelli et al. | 181/113 |
| 4,745,920 | 5/1988 | Forssmann et al. | 128/24 EL |
| 4,763,652 | 8/1988 | Brisson et al. | 128/24 EL |
| 4,834,074 | 5/1989 | Reichenberger | 128/24 EL |
| 4,928,671 | 5/1990 | Reichenberger et al. | 128/24 EL |
| 4,998,528 | 3/1991 | Erhardt | 128/24 EL |
| 5,040,537 | 8/1991 | Katakura | 128/24 AA |
| 5,054,469 | 10/1991 | Ishida | 128/24 EL |
| 5,095,891 | 3/1992 | Reitter | 128/24 EL |

Primary Examiner—Lee S. Cohen
Assistant Examiner—Krista M. Pfaffle
Attorney, Agent, or Firm—Townsend and Townsend, Khourie and Crew

[57] ABSTRACT

Apparatus for triggering shock waves for therapeutic purposes, and generated with the aid of spark discharge in a liquid includes a signal analyzer disposed for receiving the ECG signal from a patient, a pulse generator being connected to this analyzer for sending a trigger signal shortly after the occurrence of the R peak in the ECG signal. An electromagnetically manoeuvreable, moving auxiliary electrode (14) is disposed for motion towards or into a fixed electrode gap (8, 10) in response to the trigger signal for connecting the spark gap (4, 6) to high voltage by making the electrode gap conductive.

6 Claims, 2 Drawing Sheets

Vulnerable period

APPARATUS FOR TRIGGERING SHOCK WAVES

The present invention relates to an apparatus for triggering shock waves used for therapeutic purposes.

The invention thus relates to apparatus for triggering shock waves generated with the aid of spark discharge in a liquid synchronously with the heart ECG in connection with extracorporal comminution of calculi, e.g. gall stones or kidney stones.

The apparatus includes a signal analyzer, which filters through the R peaks in the patient's ECG. The analyzer is connected to a pulse generator, which creates a trigger pulse for each detected R peak. The respective shock wave is triggered with the aid of this trigger pulse. Using this procedure the shock waves will not occur at the vulnerable period of the ECG cycle, i.e. the shock wave will be in the part of the heart beat where the heart has not had time to be repolarized after its latest activity, see FIG. 1 depicting the typical appearance of an ECG. Utilizing the R peak in conjunction with triggering shock waves is already known, e.g. from EP-A1-0 081 051.

In FIG. 2 there is shown an already known, usual embodiment of the discharge circuit. A low-inductive capacitor C is charged with a suitably selected high tension DC voltage via a resistor R or a current limiter arranged in some other way. The maximum charging current must be sufficiently high to enable charging the capacitor C fully before each new shock wave. If it is assumed that the patient's pulse is 1 Hz (60 beats/minute), each heart beat takes 1,000 ms, i.e. the time between R peaks for this patient is 1,000 ms. The capacitor C is also connected in series with a first spark gap 8, 10 in the triggering apparatus, and is furthermore connected in series with a second spark gap 4, 6, which is placed in one focus of the ellipsoidal reflector 2 used in the type of apparatus in question for comminuting calculi. When flashover occurs at the gap 8, 10 there is obtained an extremely rapid voltage build-up at the second spark gap 4, 6 in the ellipsoid, and the liquid inside it is gasified very rapidly, like an explosion, the shock wave thus being generated. This type of apparatus is described in the Swedish patent application 8900994-8 filed concurrently with this application. Too slow voltage build-up at the second spark gap 4, 6 results in the worst case in a resistive discharge of the capacitor C or to a shock wave having an unsuitably slow pressure front. In the type of apparatus in question, a voltage derivative is desired where the voltage attains its maximum value in about 8.5 microseconds. This is a condition for generating a shock wave which will effectively disintegrate calculi.

The trigger spark gap in this previously known apparatus thus includes two spherical balls 8, 10 of which one 8 is connected to the high voltage pole of the spark gap in the liquid. These balls are arranged at a mutual spacing such that spontaneous flashovers normally do not occur, irrespecxtive of air pressure and humidity.

An auxiliary electrode 12 is arranged in or adjacent the electrode gap between electrodes 8 and 10. As a response to the occurrence of the R peak a high voltage is applied via a high-ohmic resistor $R_1$ to this auxiliary electrode 12, irrespective of the feed voltage to the capacitor C, so that an avalanche ionizing spark is generated in the area between the electrodes 8, 10 and the electrode gap will be conductive, the capacitor C being discharged across the gap 4, 6 for generating a shock wave. With this arrangement the avalanche ionizing spark is generated sufficiently rapidly after a detected R peak for the shock wave in the reflector 2 to be triggered with a sufficiently short lag, which does not exceed some milliseconds after the R peak maximum.

A drawback with this known technique is that it is sensitive to air pressure and humidity, which requires conditioning the trigger circuit environment by placing it in a nitrogen gas atmosphere, and it has been found difficult to make it function satisfactorily for different voltages across the capacitor C.

The object of the present invention is to eliminate these drawbacks of the previously known technique and to provide an apparatus for triggering shock waves by spark discharge for therapheutic purposes which does not require a special, conditioned environment, using nitrogen gas or the like, thus signifying an important simplification with accompanying cost savings as well as trouble-free function within a large voltage interval.

This object is achieved with an apparatus of the kind mentioned in the introduction and having the characterizing features disclosed in claim 1.

In the inventive apparatus, there is thus used a moving auxiliary electrode, and in a preferred development of the apparatus in accordance with the invention this electrode is a ball which is partially hollow for reducing its weight.

It should be noted that the fixed electrodes of the trigger gap as well as the moving auxiliary electrode are made as comparatively large balls, the diameter being typically of the order of magnitude of 1.5 cm, enabling a field charge ($kV/m^2$) which is sufficiently low that undesired, spontaneous flashovers between the electrodes are already avoided at relatively moderate electrode spacing.

In accordance with a still further advantageous embodiment of the apparatus in accordance with the invention, a filter means is connected to the signal analyzer for detecting the R peaks in the ECG signal, this means inhibiting triggering signals when interference in the ECG signal is too great.

An embodiment of the invention apparatus selected as an example will now be described in more detail in connection with FIGS. 3 and 4.

Figure 1:
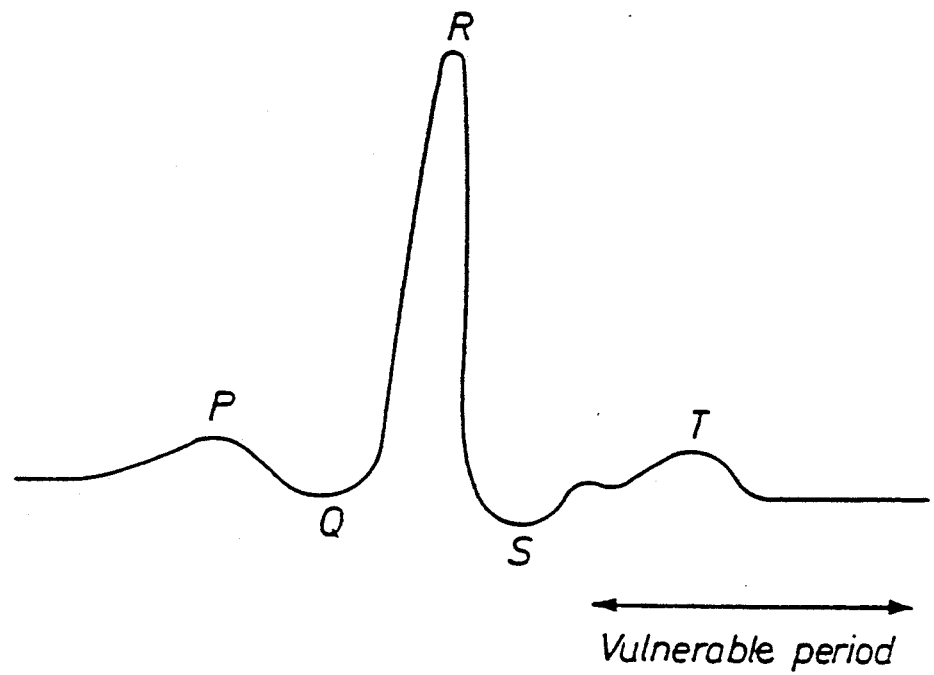
FIG. 1 illustrates the qualitative appearance of the ECG signal.
Figure 2:
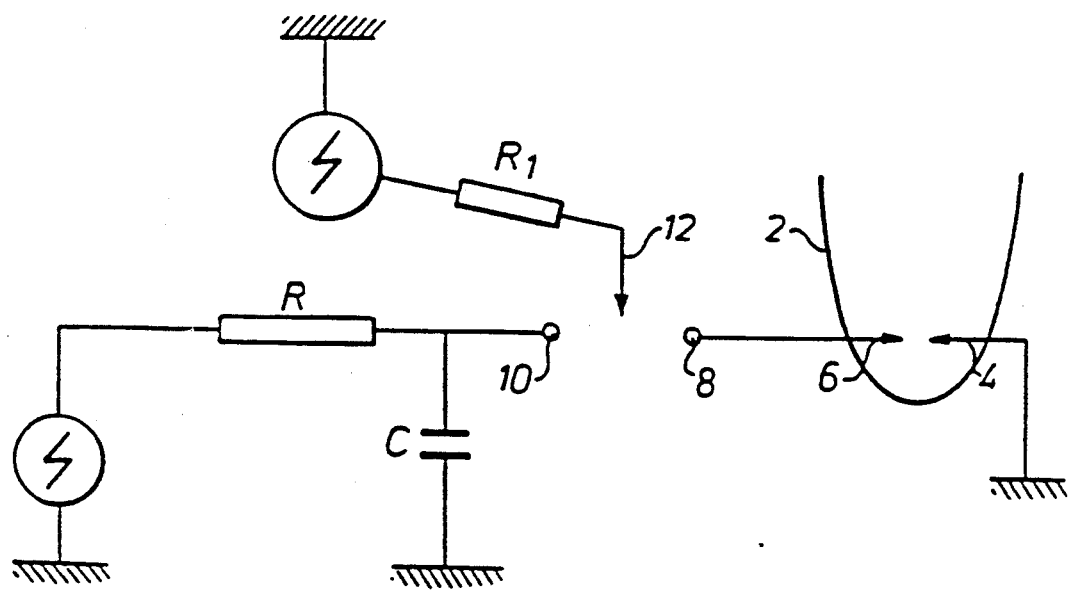
FIG. 2 illustrates a triggering apparatus in accordance with previously known technique.
Figure 3:
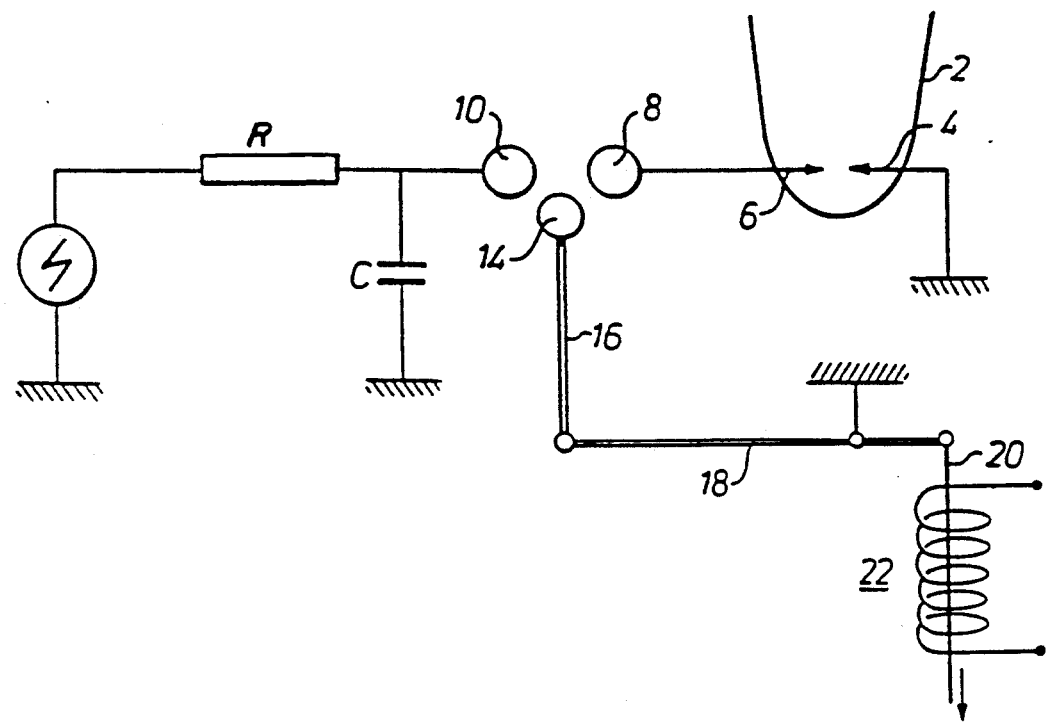
FIG. 3 illustrates an example of the apparatus in accordance with the invention and FIG. 4 is a block diagram of an associated electric circuit.

In FIG. 3, corresponding details as in the apparatus according to FIG. 2 have been given the same reference denotations.

In the embodiment in accordance with the invention, the auxiliary electrode is made movable and comprises a partially recessed ball 14 carried by a titanium rod 16, which is maneuverable by a solenoid 22 via a linkage system 18, 20 for moving the auxiliary electrode in towards the electrodes 8, 10, see FIG. 3. The auxiliary electrode 14 is electrically freely floating.

Figure 4:
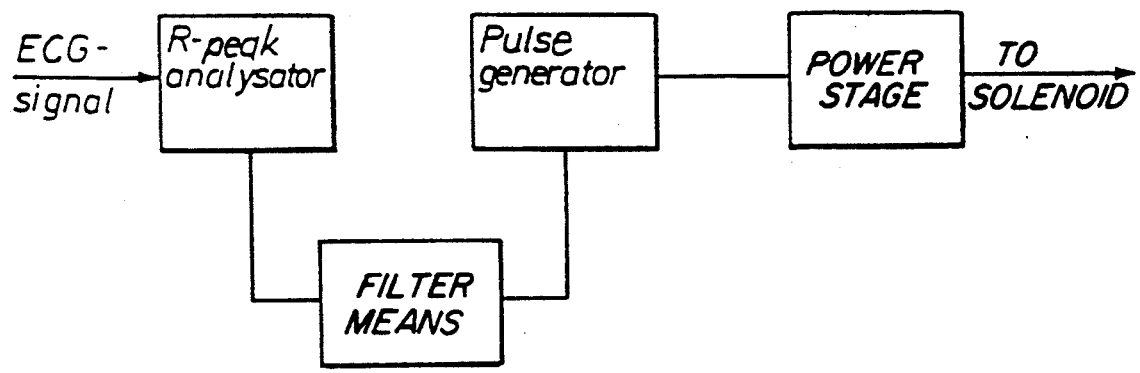

A pulse generator is connected to an R peak analyzer which detects the occurrence of the R peak, the pulse generator being intended to give a trigger signal via a power stage to the solenoid 22 in response to the occurrence of the R peak, see FIG. 4. The solenoid 22 is thus activated, causing the link 20 to move downwards in FIG. 3, which is translated into an upward movement of the auxiliary electrode 14 towards the electrodes 8, 10.

With this arrangement, the moving electrode 14 can be accelerated very rapidly towards the area between the two fixed electrodes 8, 10, since it is subjected to a very heavy acceleration, from a speed of zero to 10 m/s within about 10 ms. For reasons of strength this spherical electrode 14 is therefore mounted on a titanium rod 16.

The fixed electrodes 8, 10 are suitably steel balls, while the auxiliary electrode 14 is preferably made from titanium in order to reduce its weight.

In the inventive apparatus the solenoid 22 is fed from the power step with a short pulse, typically of 12 ms length and of high power, typically 350 watts. Since the power is only applied during 1.2% of the whole cycle time for a patient with a pulse of 60 beats/minute (1Hz) the total energy supply will not be greater than that which will enable fan cooling to be used for the solenoid, which simplifies implementation.

The moving electrode 14 can be accelerated forward into mechanical contact between the fixed electrodes 10, 8 within 10 ms. These is a voltage of typically 10-30 kV across the fixed electrodes 8, 10 and flashover generating a shock wave in the reflector 2 occurs as soon as the flashover distance is reached for the three series-connected balls 8, 10, 14. This means that the shock wave is formed in the reflector 2 earlier than 10 ms after a detected R peak, and more early the higher the voltage applied to the electrodes 8, 10.

It will be understood that due to the movement of the moving electrode 14 towards the fixed electrodes 8, 10 the distance is reduced in relation to both these electrodes, thus causing the effect of doubling the speed of the moving electrode 14.

I claim:

1. An apparatus for generating shock waves for extracorporal comminution of calculi comprising:
   an electrical energy supply;
   an electrically operated shock wave generator;
   trigger means connected to an ECG-signal delivering device for generating a trigger signal in response to the occurrence of a ECG-signal characteristic;
   first and second electrodes defining an electrode gap therebetween, said first electrode being coupled to said energy supply and said second electrode being coupled to said shock wave generator;
   an auxiliary electrode movable between a conductive position, which makes said electrode gap conductive, and a non-conductive position; and
   means for displacing said auxiliary electrode responsive to said trigger signal such that upon generation of said trigger signal by said trigger means said auxiliary electrode is displaced from said non-conductive position to said conductive position so that said electrode gap is conductive.

2. The apparatus as claimed in claim 1 wherein said auxiliary electrode is free floating.

3. An apparatus as claimed in claim 1 wherein said auxiliary electrode is a partially hollow ball.

4. An apparatus as claimed in claim 1 wherein the displacing means includes an electromagnet, a linkage system and a rod, said auxiliary electrode being disposed at one end of said rod, said rod being connected to said linkage system and being displaced to said conductive position by said electromagnet via said linkage system when said trigger signal is supplied to said electromagnet.

5. An apparatus as claimed in claim 4 wherein said auxiliary electrode is displaced into contact with said first and said second electrodes, when the trigger signal is supplied to said electromagnet.

6. Apparatus as claimed in claim 1 wherein the trigger means includes a signal analyzer for receiving said ECG-signal and a filter means connected to said signal analyzer for inhibiting the deliverance of said trigger signal when interference in said ECG-signal exceeds a predetermined level.

* * * * *